United States Patent [19]

Wilkerson

[11] Patent Number: 4,948,813

[45] Date of Patent: Aug. 14, 1990

[54] BENZYLKETONE PHOSPHOLIPASE $A_2$ INHIBITORS

[75] Inventor: Wendell W. Wilkerson, New Castle, Del.

[73] Assignee: E. I. Du Pont de Nemours and Company, Wilmington, Del.

[21] Appl. No.: 386,530

[22] Filed: Jul. 28, 1989

Related U.S. Application Data

[63] Continuation-in-part of Ser. No. 126,618, Nov. 30, 1987, abandoned.

[51] Int. Cl.$^5$ .............................................. A61K 31/35
[52] U.S. Cl. .................................... 514/648; 514/649; 514/576; 564/321; 564/342; 564/344; 564/345; 562/45

[58] Field of Search ............... 564/336, 367, 321, 342, 564/344, 345; 514/649, 654, 576, 648; 562/45

[56] References Cited

U.S. PATENT DOCUMENTS 3,979,444  9/1976  Lednicer ............................. 260/490
4,239,780  12/1980  Wallach ............................. 424/330

Primary Examiner—John M. Ford
Assistant Examiner—Zinna Northington Davis

[57] ABSTRACT

The invention relates to benzylketone phospholipase $A_2$ inhibitors, pharmaceutical compositions containing them, and methods of treating phospholipase $A_2$-mediated conditions in mammals by administration of a therapeutically effective amount of such a benzylketone phospholipase $A_2$ inhibitor. These compounds are also intermediates in the synthesis of other $PLA_2$ inhibitors.

26 Claims, No Drawings

BENZYLKETONE PHOSPHOLIPASE A2 INHIBITORS

This is a continuation-in-part of application Ser. No. 071,126,618, filed Nov. 30, 1987, now abandoned.

BACKGROUND OF THE INVENTION

This invention relates to benzylketones and processes for their preparation, pharmaceutical compositions containing them and pharmaceutical methods using them. These compounds have shown activity as inhibitors of the enzyme phospholipase $A_2$. They are also intermediates in the synthesis of other $pLA_2$ inhibitors.

The important role of phospholipase $A_2$ in the biosynthesis of prostaglandins and leukotrienes indicates that inhibitors of phospholipase $A_2$ may be valuable therapeutic agents having wide applicability in inflammatory, allergic and other phospholipase $A_2$ mediated conditions in mammals. Although some currently available anti-inflammatory agents show activity against phospholipase $A_2$ or other enzymes of the "arachidonic acid cascade", there is a continuing need for safer and more effective drugs capable of treating inflammatory and/or allergic diseases.

U.S. Pat. No. 4,239,780 (issued to D. P. Wallach on Dec. 16, 1980) discloses the use for treating pbospholipase $A_2$ mediated conditions of compounds of the formula:

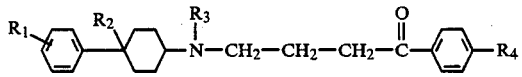

wherein $R_1$ is 4—Cl, 4—$CF_3$, H, or 2—or 4—$CH_3$;
$R_2$ is $CH_3$—O—, —$CH_2$—OH, or H;
$R_3$ is H or $CH_3$; and
$R_4$ is F or Cl.

These compounds and their activities as inhibitors of phospholipase $A_2$ are also described in D. P. Wallach and V. J. R. Brown, *Biochemical Pharmacology*, 30, 1315 (1981).

SUMMARY OF THE INVENTION

It has been discovered that benzylketones of Formula I are phospholipase $A_2$ inhibitors and are useful in treating inflammation and other phospholipase $A_2$ mediated conditions in mammals. It has also been demonstrated that compounds of Formula I are useful as pharmaceutical and agricultural intermediates.

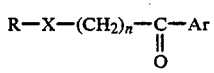

where
Ar is

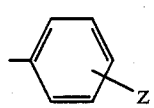

where
Z is H, F, Cl, Br, OH, $OR^1$, $S(O)_mR^1$, and
$R^1$ is methyl or ethyl, and m is 0 or 2;
n is 2 to 5;
X is NH, $NR^2$, O, $S(O)_p$, and $R^2$ is methyl or ethyl, and p is 0, 1, or 2;
R is $C_6$-$C_{25}$ alkyl, pyridyl, aryl or substituted aryl of the formula:

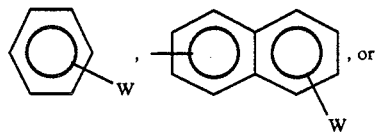

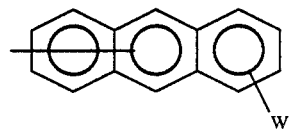

where W is H, F, Cl, Br, hexafluoroisopropanol, phenyl, $C_1$-$C_{18}$ alkyl. $OR^3$, $SR^3$, and $R^3$ is methyl or ethyl;
or R is benzhydryl, phenyl-(4-pyridyl)methyl, or $C_7$-$C_{25}$ alkaryl or substituted alkaryl where the substitution is on the aromatic moiety and is F, Cl, Br, $OR^3$, $S(O)_rR^3$, or $C_1$-$C_{10}$ alkyl, Cl, Br, OR, $S(O)_rR^3$, or $C_1$-$C_{10}$ alkyl, where $R^3$ is methyl or ethyl, and r is 0, 1, or 2;
provided that
a. when X is N-$CH_3$ or N-$C_2H_5$, R must be hydroxyhexafluoroisopropylphenyl;
b. when X is 0, n can not be 2;
c. when X is $S(O)_p$, W cannot be methyl or ethyl;
d. when X is NH, R cannot be phenyl, benzyl, 1-methylbenzyl, phenethyl, substituted phenylethyl, or pyridyl; and
e. when R is benzhydryl. Z must be F.

The preferred compounds of this invention are those compounds of Formula I described above where Ar is phenyl or substituted phenyl

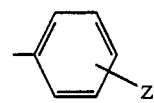

where
Z is F, Cl, OH, $OR^1$, $S(O)_mR^1$, and
$R^1$ is methyl or ethyl, and m is 0 or 2;
n is 2 to 5;
X is NH or $S(O)_p$, and p is 0 or 2; R is C6-C25 alkyl, pyridyl, aryl, or substituted aryl of the formula:

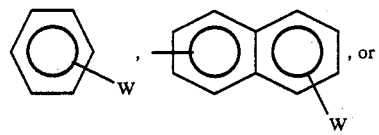

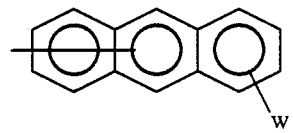

where

W is H, hexafluoroisopropanol, phenyl,
$C_1$-$C_{14}$ alkyl, $OR^3$, or $SR^3$; where
$R^3$ is methyl or ethyl;
or R is 2-naphthalenylethyl, debydroabietyl, phenyl-(4-pYridyl)methyl, 4-methoxyl-naphthalenylmethyl, benzyl, 6-methoxy-2-naphthalenylethyl, 1-naphthalenylethyl, 1-naphthalenylmethyl, benzhydryl, or 1-benzyl-4-pyridinyl-ethyl.
provided that when
X is NH, R cannot be pyridyl and $R^3$ cannot be methyl or ethyl.

More preferred compounds of the invention are those compounds of Formula I described above where
Ar is phenyl, 4-fluorophenyl, 4-methoxyphenyl, or 4-methylthiophenyl:
n is 2 or 3;
X is NH or S;
R is 4-(hexafluoroisopropyl)phenyl, cyclohexane methyl, myrtanyl, 2-naphthalenylethyl, 1-naphthalenylethyl, 2-methylphenyl, 3-methylphenyl, 4-methylphenyl, hexyl, heptyl, octyl, decyl, undecyl, dodecylphenyl, tetradecyl, hexyldecyl, octadecyl, phenyl-(4-pyridyl)methyl, 4-tert-butylphenyl, 4-n-butylphenyl, 4-n-hexy)phenyl, 4-decylphenyl, 4-dodecylphenyl, 6-methoxy-2-naphthalenylethyl, 4-methoxy-I-naphthalenylmethyl, 4-biphenylmethyl, dehydroabietyl, or 4-pyridyl; 2-(1-adamantyl)ethyl, 1-methyl-1-(1-adamantyl)-methyl.
provided that when
X is NH, R cannot be 2-, 3-, or 4-methylphenyl, or 4-pyridyl.

The compounds of Formula I that are specifically preferred for reasons of biological activity are:
a. 1-(4-Fluorophenyl)-3-[(phenyl)(4-pyridyl)methylamino]-1-propanone Dihydrochloride.
b. 1-(4-Fluorophenyl)-3-(undecylamino)-1-propanone Hydrochloride.
c. 1-(4-Fluorophenyl)-3-(decylamino)-1-propanone Hydrochloride.
d. 4-([1,4a-Dimethyl-1,2,3,4,4a,9,10,10a-octahydro-7-(1-methylethyl)-1-phenanthrenyl]-methylamino]-1-(4-fluorophenyl)-1-butanone 4-Methylbenzene sulfonate.
e. 1-(4-Fluorophenyl)-3-([1,4a-dimethyl-7-(1-methylethyl)-1,2 3,4 4a,9,10,10a-octahydro-1-phenanthrenyl-1-yl]methylamino]-1-propanone 4-Methylbenzene sulfonate.
f. 1-(Fluorophenyl)-4-(3-methylphenylthio)-1-butanone.
g. 1-(Fluorophenyl)-4-(4-methylphenylthio)-1-butanone.

DETAILED DESCRIPTION OF THE INVENTION

The compounds of this invention have demonstrated pharmacological activitY as inhibitors of the enzyme phospholipase $A_2$ ($PLA_2$). Phospholipase $A_2$ acts to release arachidenic acid from pbospholipids. Once released, arachidonic acid is rapidly metabolized by a variety of enzymes of the "arachidonic acid cascade". The products of the arachidonic acid cascade include prostaglandins, leukotrienes, and related compounds. These compounds exhibit a remarkably broad spectrum of biological activity, and inhibition of their biosynthesis is recognized as a valuable mechanism for production of anti-inflammatory effects.

Both prostaglandins and leukotrienes are believed to have important functions as mediators of inflammation and currently available drugs which inhibit their production are of significant therapeutic value in man and other mammals. Nonsteroidal anti-inflammatory agents such as the salicylates act as inhibitors of prostaglandin synthesis from arachidonic acid by inhibiting the cyclooxygenases. This inhibition of prostaglandin synthesis is believed to be the basis for many of the therapeutic effects of the aspirin-like drugs. The anti-inflammatory activity of the glucocorticosteroids, on the other hand, is believed to be at least partly due to their ability to induce the biosynthesis of a phospholipase $A_2$ inhibitor protein, thereby diminishing the release of arachidonic acid from phospholipids, by decreasing concentrations of arachidonic acid the substrate for the entire arachidonic acid cascade, production of leukotrienes as well as prostaglandins can be decreased, Many diseases and conditions in man and other mammals have inflammatory and/or allergic components believed to bed mediated by phospholipase $A_2$, e.g., rheumatoid arthritis and other rheumatic disorders various collagen diseases, dermatoses, psoriasis, hypersensitivity and immune reactions, bronchospastic diseases such as asthma, and disorders of platelet aggregation. Because the compounds of this invention have shown activity as $PLA_2$ inhibitors, valuable pharmacological activity in these and other diseases or conditions mediated by the various products of the arachidonic acid cascade is to be expected.

Synthesis

The compounds of this invention can be illustrated by Formula I.

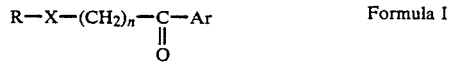

These compounds can be prepared by alkylating an amine (X=NH), alcohol (X=O), or thiol (X=S) with a haloalkylphenone or its ketal, or an α,β-unsaturated ketone as shown in Equation 1.

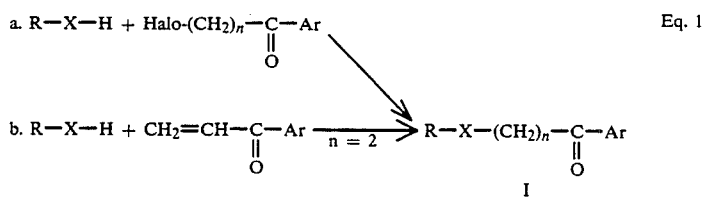

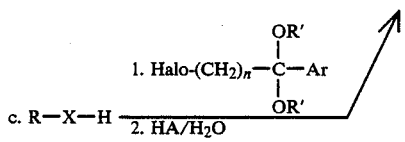

Alternatively, when n=2, the ketone (I) can be prepared by employing the Mannich Reaction as described by F. F. Blicke, *Organic Reactions*, 1(10), 303 (1942). This reaction involves the reaction of a primary amine hydrochloride, formaldehyde, and an acetophenone to give a β-aminoketone as illustrated in Equation 2.

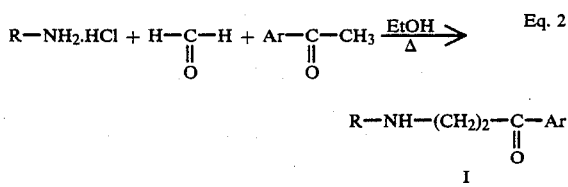

Compounds of Formula I where X is S(O)p and where p is 1 or 2 can be prepared from compounds of Formula 1 where X is S by selective oxidation with meta-chloroperbenzoic acid at reduced temperatures, or OXONE (2KHSO$_5$.KHSO$_4$.K$_2$SO$_4$) respectively.

When X is NH or the molecule contains an amine, the compounds of Formula I may be isolated as the "free base" or as pharmaceutically acceptable salts of such acids as hydrochloric acid, hydrobromic acid, sulfuric acid, phosphoric acid, acetic acid, formic acid, citric acid, p-toluenesulfonic acid, or tartaric acid.

The compounds of Formula I may be isolated as asymmetric molecules, or as raoemates, or optically pure molecules depending on the nature of the starting material(s).

The compounds of the invention and their synthesis are further illustrated by the following examples. All temperatures are in degrees Celsius. Solvent ratios for thin-layer chromatography (tlc) are by volume.

EXAMPLE 1

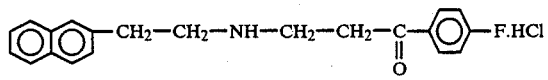

1-(4-Fluorophenyl)-3-[2-(2-naphthalenyl)-ethylamino]-1-propanone Hydrochloride

Method A.

A solution of 2-naphthaleneethylamine hydrochloride (20.8g, 0.1 mole) and sodium hydroxide (4.4g, 0.11 mole) in tetrahydrofuran-water (3:1, 100 ml) was treated dropwise with a solution of 3-chloro-4'-fluoropropiophenone (18.7g, 0.1 mole) and stirred at room temperature for 16 hours. The mixture was treated with 1N hydrochloric acid and concentrated in vacuo. The residue was triturated with water (400 ml) and the resulting solid was collected by filtration, washed with water and diethyl ether, and dried. The product was recrystallized from ethanol to yield the title compound (25.5 q, 71%); mp 206.5°–208°; IR(nujol): C=O @ 1680 cm.$^{-1}$; NMR(DMSO-d$_6$, TMS): δ 3.1–3.9(m,8H,C-H$_2$—CH$_2$—N—CH$_2$—$_{CH_2}$), 7.0–8.2(m,11H, aromatic). Anal. Calcd. for C$_{21}$H$_{20}$FNO=·HCl, MW 357.85: C,70.48; H,5.96; N,3.92. Found: C,70.39; H,6.01; N,3.93. Mass spectrum m/e 321.

Method B.

A solution of 3-chloro-4'-fluoropropiophenone (9.3 g, 0.05 mole) in 100 ml THF was treated with triethylamine (5.6 g, 0.055 mole) and stirred at room temperature for one hour. The mixture was treated with 2-naphthaleneethylamine hydrochloride (10.4 g, 0.05 mole) and refluxed for six hours. The reaction mixture was cooled to room temperature, and the resulting crystals were collected by filtration, washed with THF, ether, and water: and dried to give a tlc (chloroform-methanol, 9:1) homogeneous title compound (17.2 g, 96%); mp 208°–210°; IR(nujol): C=O @ 1675 cm$^{-1}$; NMR(DMSO-d$_6$, TMS): δ 3.20(t.2H,CH$_2$—CO), 3.37(m,4H,Ar—CH$_2$—CH$_2$), 3.60(t,2H,N—CH$_2$), [7.3–7.6(m,5H), 7.7–7.8(m,2H), 8.10(m,2H) aromatic]; Anal. Found: C,70.37; H,5.92; N,3.81. Mass spectrum m/e 321,184.

Method C. A mixture of naphthaleneethylamine hydrochloride (11.4 g, 0.055 mole), formalin (3.0 g, 0.1 mole), and 4-fluoroacetophenone (6.9 g, 0.05 mole) in 50 ml of EtOH was refluxed for 24 hours. The mixture was diluted with 200 ml of 1N HCl, and the resulting solid was collected by filtration, washed with a mixture of THF-Et$_2$O (1:1), and dried. The solid was recrystallized from EtOH to yield the title compound 6.2 g, 32%); mp 208°–210°.

EXAMPLE 2

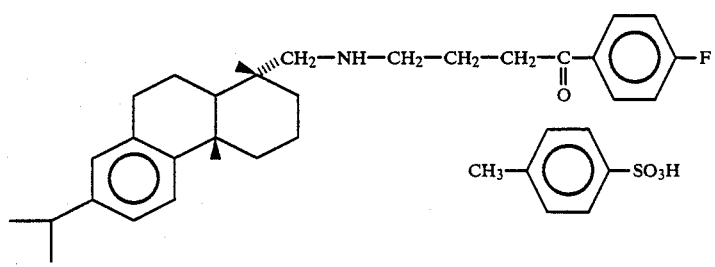

4-([1,4a-Dimethyl-1,2,3,4,4a,9,10,10a-octahydro-7-(1-methylethyl)-1-phenanthrenyl]-methylamino-1-(4-fluorophenyl)-1-butanone 4-Methylbenzenesulfonate A mixture of 4-chloro-4'-fluorobutyrophenone-2,2-dimethylpropylene ketal (28.7 g, 0.1 mole), dehydroabietylamine (28.5g, 0.1 mole), potassium carbonate (4 g, 0.35 mole), and potassium iodide (1 g) in DMF (200 ml) was heated at reflux for 24 hours and concentrated in vacuo. The residue was partitioned between ether (300 ml) and water (200 ml). The organic phase Was washed with brine, dried over MgSO4, filtered, and concentrated in vacuo to an oil. The oil was dissolved in MeOH (300 ml) and conc. HCl (50 ml) and stirred until no ketal was evidenced by tlc (CHCl3-MeOH, 9:1). The organic solvent was removed in vacuo, and the aqueous phase was made alkaline (pH 8) with 2N NaOH. The mixture was extracted with CH2Cl2(300 ml). The organic phase was washed with water and brine, dried over MgSO4, filtered, treated with p-toluenesulfonic acid monohydrate, and concentrated in vacuo. The residue was triturated with ether (400 ml) and the resulting solid was collected by filtration, washed with ether, and dried to yield the title compound (43.3g, 70%); mp 166°–167°; IR(nujol): C=O @ 1687 cm$^{-1}$; NMR(CDCl3, TMS): δ 35 aliphatic protons and 11 aromatic protons; Anal. Calcd. for C30H40FNO.C7H8O3S, MW 621.85: C,71.46; H,7.78; N,2.25; S,5.16. Found: C,71.63; H,7.93; N,2.18; S,5.23. Mass spectrum (FAB) m/e 450 (M+1); [α]$_D^{25}$ +20.3(c,1.05,MeOH).

EXAMPLE 3

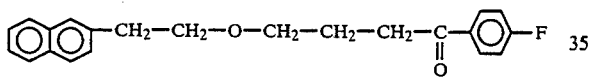

1-(4-Fluorophenyl)-4-[2-(2-naphthalenyl)ethoxy]-1-butanone

A suspension of 4-chloro-4'-fluorobutyrophenone-2,2-dimethylpropylene ketal (28.7 g 0.1 mole) and sodium hydride (2.6 g, 0.11 mole) in dry N,B-dimethylformamide (50 ml) was treated dropwise with a solution of 2-naphthalene ethanol (17.2 g, 0.1 mole) in dry N,N-dimethylformamide (50 ml). The reaction mixture was stirred at room temperature for one hour and heated at reflux under dry nitrogen for 16 hours. The mixture was concentrated in vacuo, and the residue was partitioned between diethyl ether (200 ml) and 5% sodium bicarbonate (200 ml). The organic layer was washed with brine, dried over anhydrous magnesium sulfate, filtered, and concentrated to an impure oil as indicated by tlc (chloroform-methanol, 9:1). The impure ketal was dissolved in methanol (100 ml) and treated with concentrated hydrochloric acid (50 ml) and stirred at room temperature until no starting ketal was evidenced by tlc (chloroform-methanol, 9:1). The reaction mixture was diluted with water (200 ml) and extracted with diethyl ether (200 ml). The etheral extract was Washed With brine, dried over anhydrous magnesium sulfate, filtered and concentrated to an oil. The oil was column chromatographed on silica gel (n-butyl chloride), Appropriate fractions were combined and concentrated in vacuo. The solid was recrystallized from ethanol to yield the title compound (21.2 g, 63%); mp 68°-70°; IR(nujol): C=O @ 1679 cm$^{-1}$; NMR(CDCl3, TMS): δ 2.0(d of t,2H,CH2), 2.93 (t,2H,CH2—CO), 3.03(t,2H,ArCH2), 3.53,3.73 (2t,4H,CH2—O—CH2), 6.9–8.0(m,11-H,aromatic); Anal. Calcd. for C22H21OF2, MW 336.40: C,78.55; H,6.92. Found: C,78.18; H,6.33. Mass spectrum m/e 336,154.

EXAMPLE 4

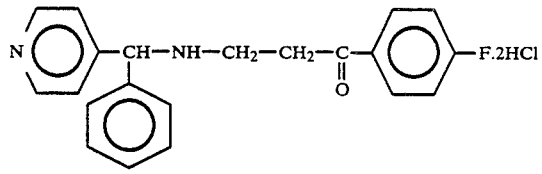

1-(4-Fluorophenyl)-3-[(phenyl)(4-pyridyl)methylamino]-1-propanone Dihydrochloride The title compound was prepared as described in Example 1A as a racemic mixture in 100% yield; mp 115° dec.

EXAMPLE 5

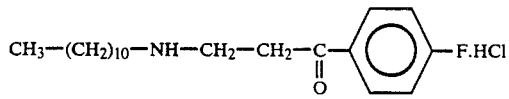

1-(4-Fluorophenyl)-3-(undecylamino)-1-propanone Hydrochloride

The title compound was prepared as described in Example 1A in 71% yield; mp 186–189° .

EXAMPLE 6

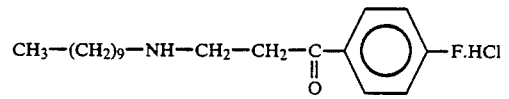

1-(4-Fluorophenyl)-3-(decylamino)-1-propanone Hydrochloride

The title compound was prepared as described in Example 1A in 67% yield; mp 183–184° ; IR(nujol): C=O @1673 cm$^{-1}$; Anal. Calcd. for C19H30FNO.HCl, MW 343.91: C, 66.35; H, 9.09; N,4.07, Found: C, 66,18; H, 9.08; N, 4.03. Mass spectrum m/e 307,180.

EXAMPLE 7

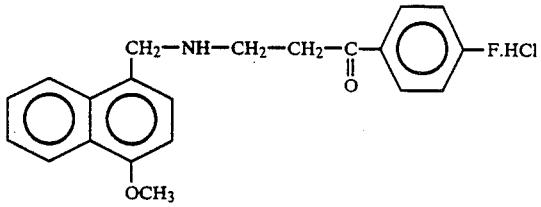

1-(4-Fluorophenyl)-3-[(4-methoxy-1-naphthalenyl)-methylamino]-1-propanone Hydrochloride The title compound was prepared as described in Example 1A in 73% yield; mp 192°–194°.

EXAMPLE 8

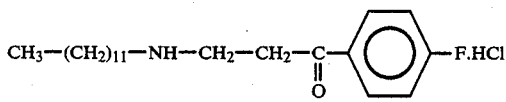

1-(4-Fluorophenyl)-3-(dodecylamino)-1-propanone Hydrochloride

The title compound was prepared as described in Example 1B in 66% yield; mp 169°–172°.

EXAMPLE 9

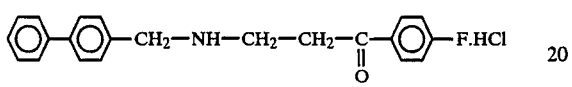

3-[(1,1-Biphenyl)-4-ylmethylamino-1-(4-fluorohenyl)-1-propanone Hydrochloride

The title compound was made by the procedure illustrated in Example 1B in 50% yield, mp 235° dec.

EXAMPLE 10

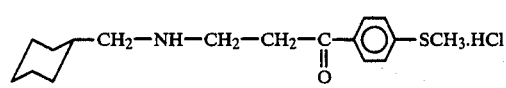

3-(Cyclohexylmethylamino)-1-(4-methylthiophenyl)-1-propanone Hydrochloride

The title compound was made by the method described in Example 1A in 81% yield; mp 186–188°.

EXAMPLE 11

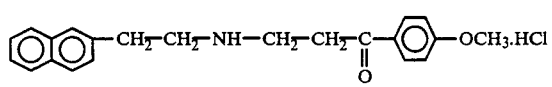

1-(4-Methoxyphenyl)-3-[2-(2-naphthalenyl)ethylamino]-1-propanone Hydrochloride

The title compound was prepared as described in Example 1A in 52% yield; mp 195.5–196.0°.

EXAMPLE 12

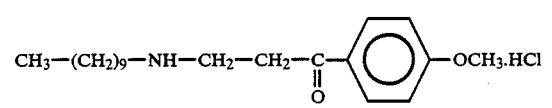

1-(4-Methoxyphenyl)-3-(decylamino)-1-propanone Hydrochloride

The title compound was synthesized as illustrated in Example 1B in 67% yield; mp 157°–158°.

EXAMPLE 13

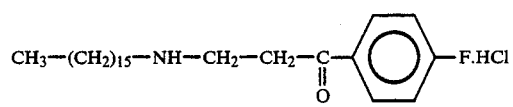

1-(4-Fluorophenyl)-3-(hexadecylamino)-1-propanone Hydrochloride

The title compound was prepared as described in Example 1B in 63% yield; mp 169°–172°.

EXAMPLE 14

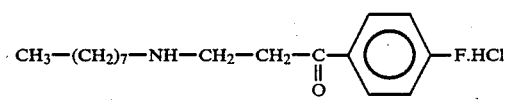

1-(4-Fluorophenyl)-3-(octylamino)-1-propanone Hydrochloride

The title compound was prepared in 19% yield using the method described in Example 1B; mp 188°–190°.

EXAMPLE 15

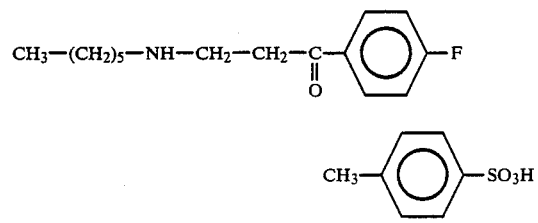

1-(4-Fluorophenyl)-3-(hexylamino)-1-propanone 4-Methylbenzene sulfonate

The title compound was prepared as described in Example 1B in 59% yield; mp 135–137°.

EXAMpLE 16

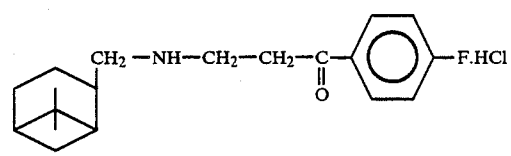

3-[(6,6-Dimethylbicyclo[3.1.1]heptan-2-ylmethyl)-aminol-1-(4-fluorophenyl)-1-propanone Hydrochloride The title compound was synthesized as illustrated in Example 1A in 82% yield: mp 229.0–229.5°; $[\alpha]_D^{25}$(c,1.00,MeOH).

EXAMPLE 17

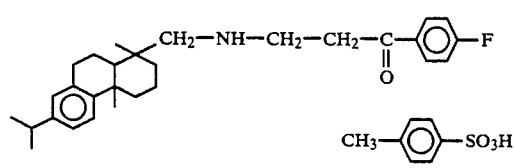

1-(4-Fluorophenyl)-3-([1,4a-dimethyl-7-(1-methylethyl)-1,2,3,4,4a,9,10,10a-octahydro-1-phenanthrenyl-1yl]methylamino)-1-propanone 4-Methylbenzene sulfonate The title compound was prepared as described in Example 1B in 48% yield; mp 157°-159°.

EXAMPLE 18

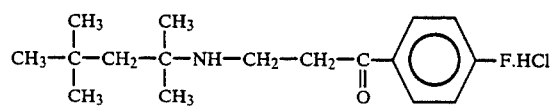

1-(4-Fluorophenyl)-4-[(1,1,3,3-tetramethylbutyl)-amino]-1-propanone Hydrochloride The title compound was prepared as described in Example 2 in 52% yield mp 231°-232°.

EXAMPLE 19

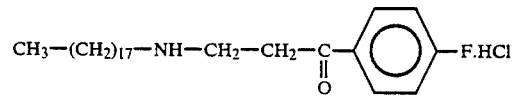

1-(4-Fluorophenyl)-3-(octadecylamino)-1-propanone Hydrochloride

The title compound was prepared as described in Example 1B in 62% yield; mp 167°-170°.

EXAMPLE 20

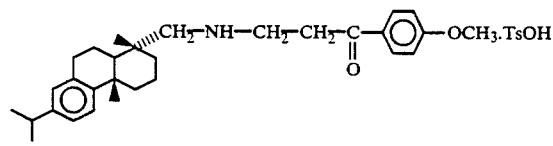

1-(4-Methoxyphenyl)-3-([4a-dimethyl-7-(1-methylethyl)-1,2,3,4,4a,9,10,10a-octahydro-1-phenanthren-1-yl]-methylamino)-1-propanone 4-Methylbenzenesulfonate The title compound was prepared as described in Example 1B in 46% yield; mp 186°-187°.

EXAMPLE 21

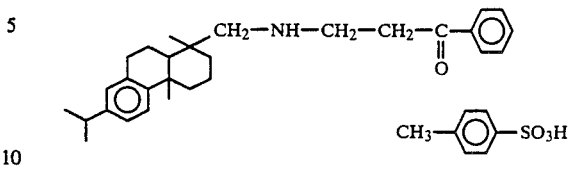

1-Phenyl-3-([4a-dimethyl-7-(1-methylethyl)-1,2,3,4,4a,9,10,10a octahydro-1-phenanthren-1-yl]-methylamino)-1-propanone 4-Methylbenzenesulfonate The title compound was prepared as described in Example 1B in 71% yield; mp 162°-164°.

EXAMpLE 22

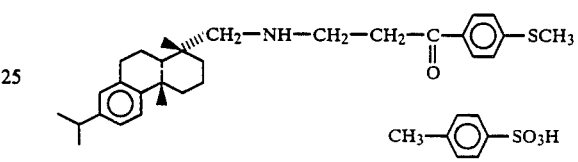

1-(4-Methylthiophenyl)-3-([4a-dimethyl-7-(1-methylethyl)-1,2,3,4,4a,9,10,10a-octahydro-1-phenanthren-1-yl]-methylamino)-1-propanone 4-Methylbenzenesulfonate The title compound was prepared as described in Example 1B in 83% yield; mp 197°-198°.

EXAMPLE 23

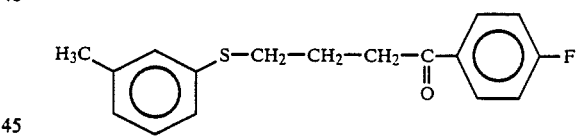

1-(Fluorophenyl)-4-(3-methylphenylthio)-1-butanone

A solution of 3-thiocresol (25 g, 0.2 mole) and 4-chloro-4'-fluorobutyrophenone (40.1 g, 0.2 mole) in tetrahydrofuran (200 ml) was treated with triethylamine (22.3 g, 0.22 mole) and heated at reflux under nitrogen for six hours. The mixture was concentrated in vacuo, and the residue was partitioned between diethyl ether (200 ml) and water (200 ml). The organic layer was washed twice with 1N sodium hydroxide (200 ml), water, and brine; dried oVer anhydrous magnesium sulfate, filtered, and concentrated to an homogeneous oil (tlc, chloroform-methanol, 9:1) of constant weight to give the title compound (58.0 g, 99%); IR(neat): C=O @1686 cm.$^{-1}$); NMR(CDCl$_3$, TMS): δ 2.10(m,2H,C-CH$_2$-C), 2.38(s,3H,CH$_3$), 3.05(d of t,4H, SCH$_2$+CH$_2$CO), 6.95-7.93(m,8H,aromatic); Anal. Calcd. for C$_{17}$H$_{17}$FOS, MW 288.38: C, 70.80; H, 5.94; S, 11.12. Found: C, 70.87; H, 6.03: S,11.12. Mass spectrum m/e 288/150.

EXAMPLE 24

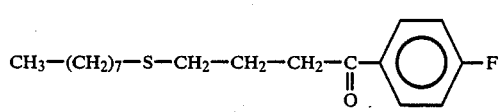

1-(4-Fluorophenyl)-4-(octylthio)-1-butanone

A mixture of 4-chloro-4'-fluorobutyrophenone-2,2-dimethylpropylene ketal (20.0 g, 0.07 mole), octanethiol (10.2 g, 0.07 mole), potassium carbonate (13.8 g, 0.1 mole) and potassium iodide (1 g) in N,N'-dimethylformamide (150 m)) was heated at reflux for six hours and concentrated in vacuo. The residue was partitioned between diethyl ether (200 ml) and water (200 ml). The organic layer was washed with water and brine, and concentrated to an oil. The oil was dissolved in methanol (150 ml) and treated with concentrated hydrochloric acid (50 ml). The mixture was heated at reflux for four hours and diluted with water (200 ml). The mixture was extracted twice with portions of diethyl ether (150 ml). The ether extracts were combined and washed with water and brine, dried over anhydrous magnesium sulfate, filtered and concentrated in vacuo to an oil of constant weight to yield the title compound (20.0 g, 93%); IR(neat): C=O @ 1687 cm$^{-1}$; NMR(CDCl$_3$, TMS): δ 0.87(t,3H,CH$_3$), 1.25(m,12H), 1.57(m,2H,CH$_2$), 2.05(m,2H,S-C-CH$_2$), 2.60(t,2H,S-CH$_2$),3.08(t,2H,S-CH$_2$), [7.10(d of d,2H) and 8.0(m,2H) p-F-phenyl]; Anal. Calcd. for C$_{18}$H$_{27}$FOS, MW 310.47: C, 69.63; H, 8.77: S 10.33. Found: C, 69.17; H, 8.49; S, 10.55, Mass spectrum m/e 310,143.

EXAMPLE 25

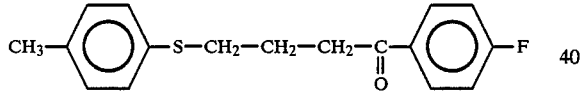

1-Fluorophenyl)-4-(4-methylphenylthio)-1-butanone

The title compound was prepared as described in Example 23 in 100% yield as an oil; IR(neat): C=O @ 1 1687 cm$^{-1}$; NMR(DMSO-d$_6$, TMS): δ 1.88(d of t,2H,CH$_2$), 2.26(s,3H,ArCH$_3$), 2.98(t,2H,CH$_2$CO), 3.16 (t,2H,SCH$_2$), [7.0–7.4(m,6H) and 7.99(m,2H) aromatic]; mass spectrum m/e 288,150.

EXAMPLE 26

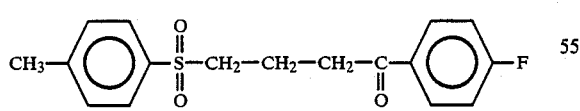

1-(4-Fluorophenyl)-4-[(4-methylphenyl)sulfonyl]-1-butanone

The title compound in Example 25 was oxidized with OXONE in methanol-water to give the title compound in 85% yield; mp 114–116°; IR(nujol): C=O @ 1965 cm$^{-1}$; NMR(DMSO-d$_6$, TMS):δ 1.85(d of t, 2H,CH$_2$), 2.42(s,3H,ArCH$_3$), 3.15(t,2H,CH$_2$CO), 3.35(t,2H,SCH$_2$), [7.34(d of d,2H) and 7.98(m,2H) p-F-phenyl], 7.48 and 7.98 (2d,4H,p-S02-phenyl); Anal. Calcd. or C$_{17}$H$_{17}$OF$_3$S, MW 320.38: C, 63.73; H,5.35; S,10.01, Found: C,63.70; H,5.30; S,9.85. Mass spectrum m/e 320.

EXAMPLE 27

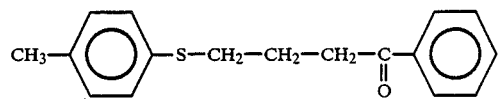

4-(4-Methylphenylthio)-1-phenyl-1-butanone

The title compound was prepared as described in Example 23 in 100% yield as an oil: IR(neat): C=O @ 1 1683 cm$^{-1}$; NMR (CDCl$_3$, TMS): δ 2.05(d of t,2H,CH$_2$), 2.30(s,3H,ArCH$_3$), 2.99(t,2H,CH$_2$CO), 3.12(t,2H,SCH$_2$), 7.0–8.0(m,9H,aromatic).

EXAMPLE 2

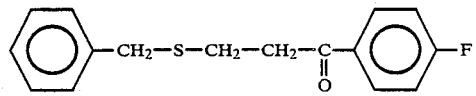

1-(4-Fluorophenyl)-3-(phenylmethylthio)-1-propanone

By substituting 3-chloro-4'-fluoropropiophenone in Example 23 the title compound was prepared in 95% yield as an oil; IR(neat): C=O @ 1700 cm$^{-1}$; NMR(DMSO-d$_6$, TMS): δ 2.73(t,2H,CH2CO), 3.30(t,2H,SCH$_2$), 3.83(s,2H,Ar-CH$_2$-S), 7.3–8.1(m,9-H,aromatic); mass spectrum m/e 274.

EXAMPLE 29

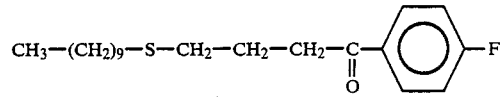

1-(4-Fluorophenyl)-4-(decylthio)-1-butanone

The title compound was prepared as described in Example 24 in 88% yield as an oil: IR(neat): C=O @ 1663 cm$^{-1}$; mass spectrum m/e 338.

EXAMPLE 30

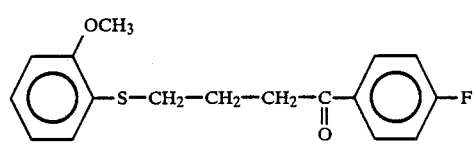

1-(4-Fluorophenyl)-4-(2-methoxyphenylthio)-1-butanone

The title compound was prepared as described in Example 23 in 100% yield; IR(neat): C=O @ 1683 cm$^{-1}$; mass spectrum m/e 288,150.

EXAMPLE 31

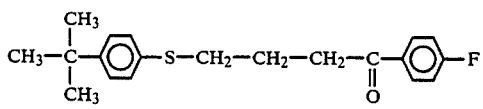

2-[4-(1,1-Dimethylethyl)phenylthio]-1-(4-fluorophenyl)-1-butanone

The title compound was prepared as described in Example 23 in 83% yield; IR(neat): C=O @ 1700 cm$^{-1}$; mass spectrum m/e 330.

EXAMPLE 32

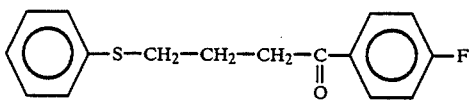

1-(4-Fluorophenyl)-4-phenylthio-1-butanone

The title compound was prepared as described in Example 23 in 96% yield as an oil; IR(neat): C=O @ 1690 cm$^{-1}$; mass spectrum m/e 274.

EXAMPLE 33

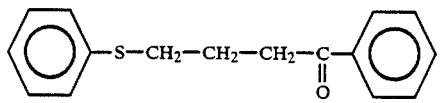

1-Phenyl-4-(phenylthio)-1-butanone

The title compound was made as described in Example 23 in 100% yield as an oil; IR(neat): C=O @ 1680 cm$^{-1}$; mass spectrum m/e 256.

EXAMPLE 34

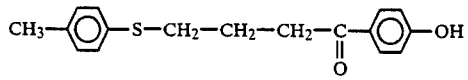

1-(4-Hydroxyphenyl)-4-(4-methylphenylthio)-1-butanone

The title compound was prepared as described in Example 23 in 91% yield as an oil: IR(neat): C=O @ 1660, OH@ 3320 cm$^{-1}$; mass spectrum m/e 286.

EXAMPLE 35

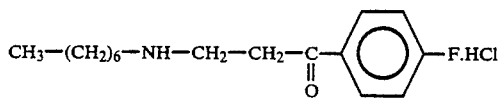

1-(4-Fluorophenyl)-3-(heptylamino-1-propanone Hydrochloride

The title compound was prepared as described in Example 1B in 38% yield: mp 188°-189°.

EXAMPLE 36

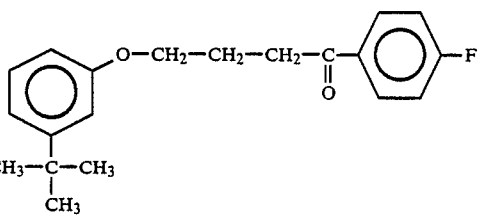

1-(4-Fluorophenyl)-4-[3-(1,1-dimethylethyl)phenylthio]-1-butanone

The title compound was prepared as described in Example 24 in 97% yield as an oil; IR(neat): C=O @ 1678 cm$^{-1}$; NMR(CDCl$_3$, TMS): δ 1.33 (s,9H,t-Bu), 2.25(d of t,2H,CH$_2$), 3.20(t,2H,CH$_2$CO), 4.08(t,2H,OCH$_2$), 6.7-8.0(m,8H,aromatics); Anal. Calcd. for C$_{20}$H$_{23}$OF$_2$, MW 314.38: C,76.40; H, 7.37. Found: C, 76.46; H, 7.44. Mass spectrum m/e 315(M,1),165.

EXAMPLE 37

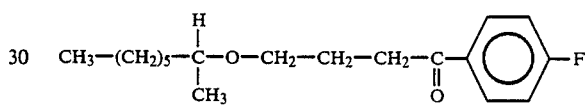

1-(4-Fluorophenyl)-4-(d-1-methylheptyloxy)-1-butanone

The title compound was prepared as described in Example 24 in 99% yield as an oil; IR(neat): C=O @ 1687 cm$^{-1}$; NMR(CDCl$_3$, TMS): δ 0.87 (t,3H,CH$_3$), 1.12(d,3H,CH$_3$), 1.1-1.7(m,12H,C$_6$H$_{12}$), 2.00(d of t,2H, CH$_2$), 3.07(t,2H,CH$_2$CO), 3.38(t,2H,OCH$_2$), 3.56(m,1H,H-C-O), [7.13 (d of d, 2H) and 8.0(m,2H) p-F-phenyl]; Anal. Calcd. for C$_{18}$H$_{27}$OF$_2$, MW 294.40: C, 73.43; H,9.24. Found: C,73.72; H, 8.98, Mass spectrum m/e 295 (M+1),165.[α]$_D^{25}$+8.69° (c,1.09,MeOH).

EXAMPLE 38

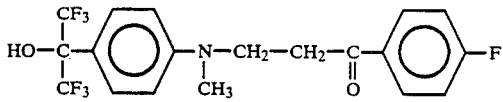

1(4-Fluorophenyl-3-([N-methyl-N-[4-(2,2,2-trifluoro-1-hydroxy(-1-(trifluoromethyl)ethyl]phenyl]amino)-1propanol The title compound was prepared as described in Example 1A in 90% yield; mp 96°-98°.

EXAMPLE 39

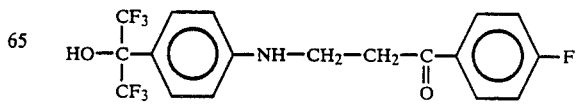

1-(4-Fluorophenyl)-3-([N-[4-(2,2,2-trifluoro-1-hydroxy)-1-(trifluoromethyl)ethyl]phenyl]amino)-1-propanone A. The title compound was prepared as described in Example 1A in 98% yield: mp 122°–123°.

B. 1-(fluorophenyl)-3-phenylamino-1-propanone was prepared as described in Example 1A in 99% yield, mp 125°–126° and treated with hexafluoroacetone trihydrate (one equivalent) in carbon tetrachloride and refluxed for 24 hours. The mixture was concentrated in vacuo, and the residue was triturated with water, collected by filtration, washed with water and dried to give the title compound in 94% yield; mp 122°–124°.

EXAMPLE 40

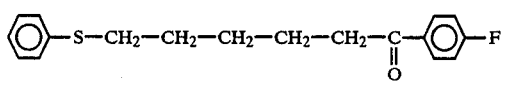

1-(4-Fluorophenyl)-6-(phenylthio)-1-hexanone

The title compound was prepared as described in Example 23 in 81% yield; IR(neat): C=O @ 1695 cm$^{-1}$; NMR(DMSO-d$_6$, TMS) δ 1.4–1.6(m,6H, CH-CH$_2$), 2.93–3.04(2t,4H,S-CH$_2$ and CH$_2$CO), 7.2–8.0(m,9H, aromatics); mass spectrum m/e 302.

EXAMPLE 41

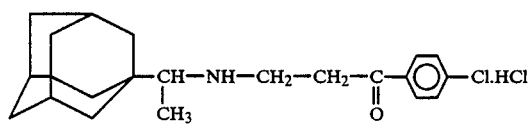

3-[1-(3-Adamantyl)ethylamino]-1-(4-chlorophenyl)-1-propanone Hydrochloride

The title compound was prepared as described in Example 1A in 98% yield; mp >300°.

EXAMPLE 42

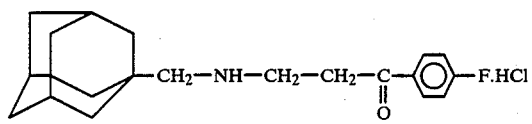

3-[(3-Adamantylmethyl)amino]-1-(4-fluorophenyl)-1-propanone Hydrochloride

The title compound was prepared as described in Example 1A in 85% yield; mp 201°–202.5°.

EXAMPLE 43

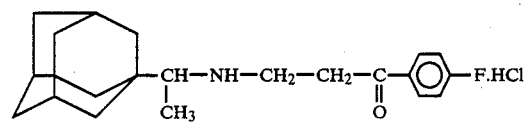

3-[1-(3-Adamantyl)ethylamino]-1-(4-fluorophenyl)-1propanone Hydrochloride

The title compound was prepared as described in Example 1A in 82% yield; mp 290° dec.

EXAMPLE 44

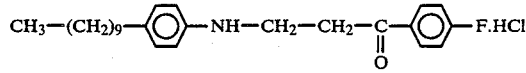

1-(4-Fluorophenyl)-3-(4-decylphenylamino)-1-propanone Hydrochloride

The title compound was prepared as described in Example 1A in 61% yield; mp 110°–111°.

EXAMPLE 45

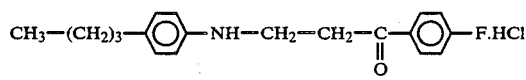

1-(4-Fluorophenyl-3-[(4-butylphenyl)amino]-1-propanone Hydrochloride

The title compound was prepared as described in Example 1A in 57% yield: mp 109°–111°.

EXAMPLE 46

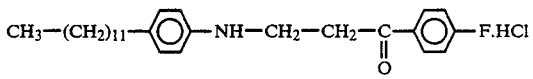

4-Fluorophenyl)-3-[(4-dodecylphenyl)amino]-1-propanone Hydrochloride

The title compound was prepared as described in Example 1A in 100% yield: mp 107°–109°.

EXAMPLE 47

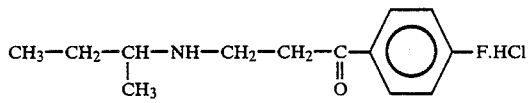

1-(4-Fluorophenyl)-3-[(1-methylpropyl)amino]-1-propanone Hydrochloride

The title compound was prepared as described in Example 1B in 72% yield; mp 164°–166°.

EXAMPLE 48

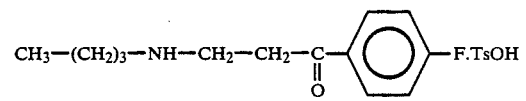

1-(4-Fluorophenyl)-3-(butylamino)-1-propanone 4-Methylbenzene sulfonate

The title compound was prepared as described in Example 1B in 66% yield; mp 130°–131°.

EXAMPLE 49

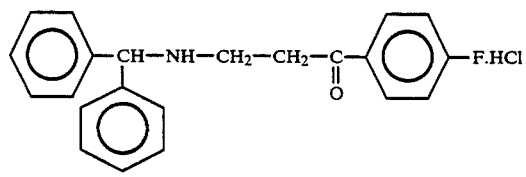

1-(4-Fluorophenyl)-3-(diphenylmethylamino)-1-propanone Hydrochloride

The title compound was prepared as described in Example 1A in 62% yield; mp 210°-214°.

EXAMPLE 50

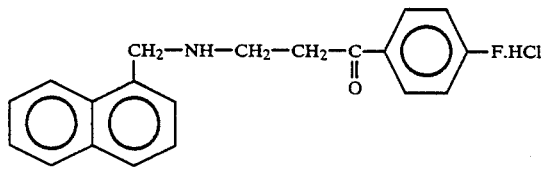

1-(4-Fluorophenyl)-3-[(1-naphthalenylmethyl)amino]-1propanone Hydrochloride

The title compound was prepared as described in Example 1A in 47% yield; mp 199°-200°.

EXAMPLE 51

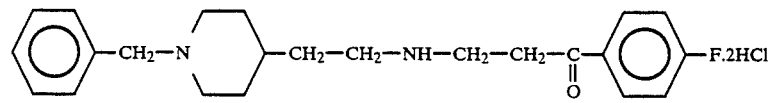

1-(4-Fluorophenyl)-3-[(1-phenylmethyl-4-piperidinyl)ethylamino]-1-propanone Dihydrochloride The title compound was prepared as described in Example 1A in 51% yield; mp 215°-217°.

EXAMPLE 52

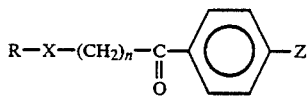

3-([1,4a-Dimethyl-1,2,3,4,4a,9,10,10a-octahydro-7-(1-methylethyl)-1-phenanthrenyl]methylamino)-1-(4-fluorophenyl)-1-propanone Hydrochloride The title compound was prepared as described in Example 1B in 58% yield as the hydrochloride salt; mp 158°-160; IR(nujol); C=O @1679 cm$^{-1}$; Anal. Calcd. for $C_{29}H_{38}FNO \cdot HCl$, MW 472.07: C, 73.78; H, 8.33; N, 2.97. Found: C, 73.70; H, 8.65; N, 3.22. Mass spectrum m/e 314(M+1),151. $[\alpha]_D^{25} + 19.44$ (c,1.00, MeOH).

The compounds synthesized according to the procedures illustrated in Examples 1 to 52 are listed in Table I. Dehydroabietyl refers to the group 1,4a-dimethyl-1,2,3,4,4a,9,10,10a-octahydro-7-(1-methylethyl)-1-methylphenanthrenylmethyl. Myrtanyl refers to the group 6,6-dimethylbicyclo[3,1,1]heptan-2-ylmethyl.

TABLE I $$R-X-(CH_2)_n-\underset{O}{\underset{\|}{C}}-\bigcirc-Z$$

| Ex | R | X | n | Z | mp | % yield |
|---|---|---|---|---|---|---|
| 1 | 2-NAPHTHALENYLETHYL | NH | 2 | F | 206.5-208 | 71 |
| 2 | DEHYDROABIETYL | NH | 3 | F | 166-167 | 70 |
| 3 | 2-NAPHTHALENYLETHYL | O | 3 | F | 68-70 | 63 |
| 4 | 4-PYRIDYL(PHENYL)METHYL | NH | 2 | F | 115 dec. | 100 |
| 5 | n-UNDECYL | NH | 2 | F | 186-189 | 71 |
| 6 | n-DECYL | NH | 2 | F | 183-184 | 67 |
| 7 | 4-METHOXY-1-NAPHTHALENYLMETHYL | NH | 2 | F | 192-194 | 73 |
| 8 | n-DODECYL | NH | 2 | F | 169-172 | 66 |
| 9 | 4-BIPHENYLMETHYL | NH | 2 | F | 235 dec. | 50 |
| 10 | CYCLOHEXYLMETHYL | NH | 2 | SCH$_3$ | 186-188 | 81 |
| 11 | 2-NAPHTHALENYLETHYL | NH | 2 | OCH$_3$ | 195.5-196 | 52 |
| 12 | n-DECYL | NH | 2 | OCH$_3$ | 157-158 | 67 |
| 13 | n-HEXADECYL | NH | 2 | F | 169-172 | 63 |
| 14 | n-OCTYL | NH | 2 | F | 188-190 | 19 |
| 15 | n-HEXYL | NH | 2 | F | 135-137 | 59 |
| 16 | (-)-cis-(MYRTANYL) | NH | 2 | F | 229-229.5 | 82 |
| 17 | DEHYDROABIETYL | NH | 2 | F | 157-159 | 48 |
| 18 | t-OCTYL | NH | 2 | F | 231-232 | 52 |
| 19 | n-OCTADECYL | NH | 2 | F | 167-170 | 62 |
| 20 | DEHYDROABIETYL | NH | 2 | OCH$_3$ | 186-187 | 46 |

TABLE I-continued

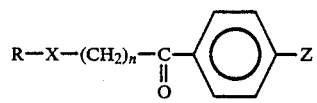

| Ex | R | X | n | Z | mp | % yield |
|---|---|---|---|---|---|---|
| 21 | DEHYDROABIETYL | NH | 2 | H | 162–164 | 71 |
| 22 | DEHYDROABIETYL | NH | 2 | SCH$_3$ | 197–198 | 83 |
| 23 | 3-METHYLPHENYL | S | 3 | F | OIL | 99 |
| 24 | n-OCTYL | S | 3 | F | OIL | 93 |
| 25 | 4-METHYLPHENYL | S | 3 | F | OIL | 100 |
| 26 | 4-METHYLPHENYL | SO$_2$ | 3 | F | 114–116 | 85 |
| 27 | 4-METHYLPHENYL | S | 3 | H | OIL | 100 |
| 28 | BENZYL | S | 2 | F | OIL | 95 |
| 29 | n-DECYL | S | 3 | F | OIL | 88 |
| 30 | 2-METHYLPHENYL | S | 3 | F | OIL | 100 |
| 31 | 4-t-BUTYLPHENYL | S | 3 | F | OIL | 83 |
| 32 | PHENYL | S | 3 | F | OIL | 96 |
| 33 | PHENYL | S | 3 | H | OIL | 100 |
| 34 | 4-METHYLPHENYL | S | 3 | OH | OIL | 91 |
| 35 | n-HEPTYL | NH | 2 | F | 188–189 | 38 |
| 36 | 3-t-BUTYLPHENYL | O | 3 | F | OIL | 97 |
| 37 | d-2-OCTYL | O | 3 | F | OIL | 99 |
| 38 | 4-HEXAFLUOROISOPRO-PANOLPHENYL | NCH$_3$ | 2 | F | 96–98 | 90 |
| 39 | 4-HEXAFLUOROISOPRO-PANOPHENYL | NH | 2 | F | 122–123 | 96 |
| 40 | PHENYL | S | 5 | F | OIL | 81 |
| 41 | ADAMANTYLETHYL | NH | 2 | Cl | >300 | 98 |
| 42 | ADAMANTYLMETHYL | NH | 2 | F | 201–202.5 | 85 |
| 43 | ADAMANTYLETHYL | NH | 2 | F | 290 dec | 82 |
| 44 | 4-n-DECYLPHENYL | NH | 2 | F | 110–111 | 61 |
| 45 | 4-n-BUTYLPHENYL | NH | 2 | F | 109–111 | 57 |
| 46 | 4-n-DODECYLPHENYL | NH | 2 | F | 107–109 | 100 |
| 47 | sec-BUTYL | NH | 2 | F | 164–166 | 72 |
| 48 | n-BUTYL | NH | 2 | F | 130–131 | 66 |
| 49 | BENZHYDRYL | NH | 2 | F | 210–214 | 62 |
| 50 | 1-NAPHTHALENYLMETHYL | NH | 2 | F | 199–200 | 47 |
| 51 | 1-BENZYL-4-PIPERI-DINE-ETHYL | NH | 2 | F | 215–217 | 51 |
| 52 | DEHYDROABIETYL | NH | 2 | F | 158–160 | 58 |

By using the methods described in the preceding examples, other compounds of Formula I can be prepared. Examples of such compounds are listed in Table II.

TABLE II

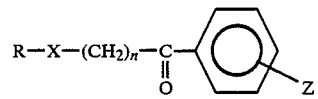

| Ex. | R | X | n | Z |
|---|---|---|---|---|
| 53 | (dehydroabietyl-CH$_2$ structure) | O | 3 | p-F |
| 54 | (dehydroabietyl-CH$_2$ structure) | S | 3 | p-F |

TABLE II-continued

R—X—(CH$_2$)$_n$—C(=O)—C$_6$H$_4$—Z

| Ex. | R | X | n | Z |
|-----|---|---|---|---|
| 55 | (dehydroabietyl CH$_2$—) | S | 2 | p-F |
| 56 | CH$_3$—(CH$_2$)$_{11}$—C$_6$H$_4$— | O | 3 | p-F |
| 57 | CH$_3$—(CH$_2$)$_{11}$—C$_6$H$_4$— | S | 3 | p-F |
| 58 | CH$_3$—(CH$_2$)$_{11}$—C$_6$H$_4$— | S | 2 | p-F |
| 59 | 2-naphthyl-CH$_2$-CH$_2$— | O | 3 | p-SCH$_3$ |
| 60 | 2-naphthyl-CH$_2$-CH$_2$— | S | 3 | p-F |
| 61 | 2-naphthyl-CH$_2$-CH$_2$— | S | 2 | p-F |
| 62 | pinanyl-CH$_2$— | O | 3 | p-F |
| 63 | pinanyl-CH$_2$— | O | 3 | p-SCH$_3$ |
| 64 | pinanyl-CH$_2$— | O | 3 | p-Br |
| 65 | pinanyl-CH$_2$— | NH | 3 | p-F |

TABLE II-continued

R—X—(CH₂)ₙ—C(=O)—⌬—Z

| Ex. | R | X | n | Z |
|-----|---|---|---|---|
| 66 | (bicyclic terpene)-CH₂— | NH | 3 | p-SO₃CH₃ |
| 67 | CH₃—(CH₂)₇-naphthyl-CH₂—CH₂— | NH | 2 | p-F |
| 68 | CH₃—(CH₂)₇-naphthyl-CH₂—CH₂— | NH | 3 | p-F |
| 69 | CH₃—(CH₂)₉-naphthyl-CH₂—CH₂— | NH | 3 | p-F |
| 70 | naphthyl-CH₂—CH₂— | NH | 3 | p-Br |
| 71 | CF₃—phenyl-cyclohexyl— | NH | 3 | p-OCH₃ |
| 72 | CF₃—phenyl-cyclohexyl— | NH | 3 | H |
| 73 | CF₃—phenyl-cyclohexyl— | NH | 3 | p-SCH₃ |
| 74 | Cl—phenyl-cyclohexyl— | NH | 2 | p-F |
| 75 | (pyridyl)(phenyl)CH— | NH | 3 | p-F |
| 76 | (pyridyl)(phenyl)CH— | S | 3 | p-F |

TABLE II-continued

R—X—(CH₂)ₙ—C(=O)—C₆H₄—Z

| Ex. | R | X | n | Z |
|---|---|---|---|---|
| 77 | pyridin-x-yl(phenyl)CH— | O | 3 | p-F |
| 78 | CH₃—(CH₂)₁₁—C₆H₄— | NH | 3 | p-F |
| 79 | (CF₃)₂C(OH)—C₆H₄— | NH | 3 | p-F |
| 80 | (CF₃)₂C(OH)—C₆H₄— | NH | 3 | p-SCH₃ |
| 81 | (CF₃)₂C(OH)—C₆H₄— | S | 3 | p-F |
| 82 | pyridin-4-yl— | S | 3 | p-SCH₃ |
| 83 | pyridin-4-yl— | S | 3 | p-OCH₃ |
| 84 | 3-CH₃—C₆H₄— | S | 3 | p-OCH₃ |
| 85 | 3-CH₃—C₆H₄— | S | 2 | p-F |
| 86 | 3-CH₃—C₆H₄— | S | 3 | p-SCH₃ |
| 87 | cyclohexyl-CH₂— | NH | 3 | p-SCH₃ |
| 88 | 4-CF₃—C₆H₄—cyclohexyl-CH₂— | NH | 3 | p-F |

TABLE II-continued

R—X—(CH₂)ₙ—C(=O)—C₆H₄—Z

| Ex. | R | X | n | Z |
|---|---|---|---|---|
| 89 | anthracen-2-ylmethyl | NH | 2 | p-F |
| 90 | anthracen-2-ylmethyl | NH | 3 | p-F |
| 91 | anthracen-2-ylmethyl | S | 3 | p-F |
| 92 | anthracen-2-ylmethyl | S | 2 | p-SCH₃ |
| 93 | anthracen-2-ylmethyl | NH | 3 | p-OCH₃ |
| 94 | dehydroabietyl (CH₂—) | NH | 2 | p-F |
| 95 | dehydroabietyl (CH₂—) | NH | 2 | p-SCH₃ |
| 96 | dehydroabietyl (CH₂—) | NH | 2 | p-OCH₃ |

TABLE II-continued

R—X—(CH₂)ₙ—C(=O)—C₆H₄—Z

| Ex. | R | X | n | Z |
|---|---|---|---|---|
| 97 | (podocarpane-type tricyclic, CH₂—) | NH | 2 | H |
| 98 | (podocarpane-type tricyclic, CH₂—) | NH | 3 | p-F |
| 99 | (dehydro tricyclic with diene, CH₂—) | O | 3 | p-F |
| 100 | (dehydro tricyclic with diene, CH₂—) | S | 3 | p-F |
| 101 | (podocarpane-type tricyclic, CH₂—CH₂—) | NH | 3 | p-F |
| 102 | (dehydro tricyclic with diene, CH₂—) | NH | 3 | p-OCH₃ |

TABLE II-continued
R—X—(CH$_2$)$_n$—C(O)—C$_6$H$_4$—Z
| Ex. | R | X | n | Z |
|---|---|---|---|---|
| 103 | 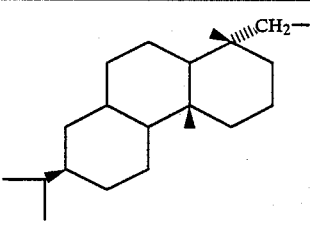 | NH | 5 | p-SCH$_3$ |
| 104 | 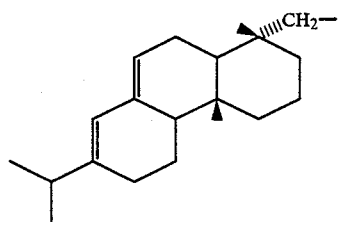 | NH | 3 | p-SCH$_3$ |
| 105 | 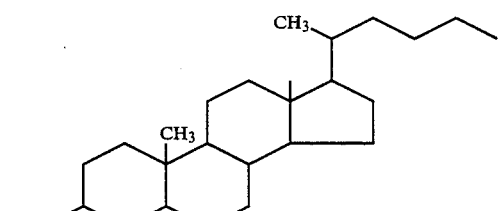 | NH | 2 | F |
| 106 | 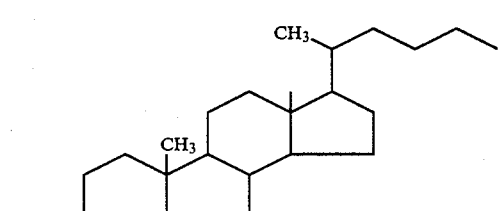 | NH | 3 | F |
| 107 | 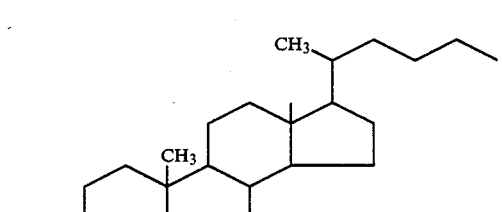 | S | 2 | F |
| 108 | 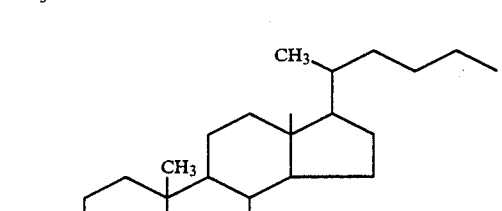 | S | 3 | F |

TABLE II-continued $$R-X-(CH_2)_n-\underset{\underset{O}{\|}}{C}-\underset{Z}{\text{C}_6H_4}$$

| Ex. | R | X | n | Z |
|---|---|---|---|---|
| 109 | 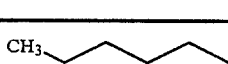 | O | 3 | F |
| 110 | 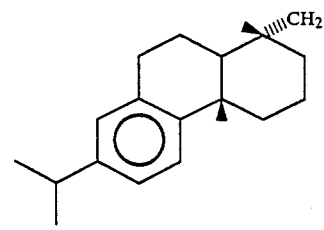 | NH | 3 | o-Cl |
| 111 | 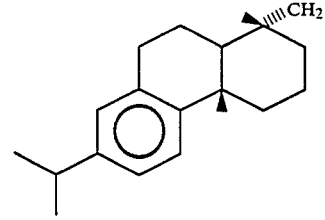 | S | 3 | o-Br |
| 112 | 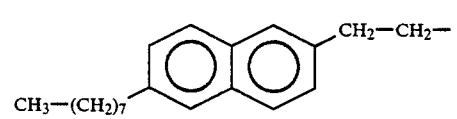 | NH | 3 | m-Cl |
| 113 | 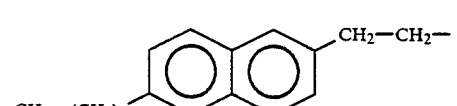 | S | 2 | m-Br |

DOSAGE AND DOSAGE FORMS

The phospholipase $A_2$ inhibitors of this invention can be administered to treat inflammatory and/or allergic conditions, including but not limited to rheumatoid arthritis, and other rheumatic disorders, collagen diseases, dermatoses, allergic diseases, chronic obstructive and bronchospastic lung diseases such as asthma and bronchitis. The compounds of this invention may also be useful in the treatment of osteoarthritis.

They may be administered by any means that enables the active agent to reach the agent's site of action in the body of a mammal. They can be administered by any conventional means available for administration of pharmaceuticals, either as individual therapeutic agents or in combination with other therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

Dosage forms (compositions) suitable for internal administration contain from about 1 milligram to about 500 milligrams of active ingredient per unit. In these pharmaceutical compositions the active ingredient will ordinarily be present in an amount of about 0.5-95% bY weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms, by inhalation in the form of a nasal spray or lung inhaler, or topically as an ointment, cream or lotion.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain the active ingredient, and, if necessary, suitable stabilizing agents, and/or, buffer substances. Anti-oxidizing agents such as sodium bisulfite sodium sulfite, or ascorbic acid either alone or combined are suitable stabilizing agents. Also used are citric acid and its salts and sodium EDTA. In addition, parenteral solutions can contain preservatives, such as benzalkonium chloride, methyl and/or propylparaben, and chlorobutanol.

Suitable pharmaceutical carriers are described in *Remington's pharmaceutical Sciences*, A. Osol, a standard reference text in this field.

Useful pharmaceutical dosage forms for administration of the compounds of this invention can be illustrated as follows:

Capsules

A large number of unit capsules are prepared by filling standard two-piece hard gelatin capsules each with 50 milligrams of powdered active ingredient, 175 milligrams of lactose, 24 milligrams of talc, and 6 milligrams of magnesium stearate.

Soft Gelatin Capsules

A mixture of active ingredient in soybean oil is prepared and injected by means of a positive displacement pump into gelatin to form soft gelatin capsules containing 50 milligrams of the active ingredient. The capsules are washed in petroleum ether and dried.

Tablets

A large number of tablets are prepared by conventional procedures so that the dosage unit is 50 milligrams of active ingredient, 6 milligrams of magnesium stearate, 70 milligrams of microcrystalline cellulose, 11 milligrams of cornstarch and 225 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is sterilized by commonly used techniques.

Suspension

An aqueous suspension is prepared for oral administration so that each 5 milliliters contain 25 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

Nasal Spray

An aqueous solution is prepared such that each 1 milliliter contains 10 milligrams of active ingredient, 1.8 milligrams methylparaben, 0.2 milligrams propylparaben and 10 milligrams methylcellulose. The solution is dispensed into 1 milliliter vials.

Lung Inhaler

A homogeneous mixture of the active ingredient in polysorbate 80 is prepared such that the final concentration of the active ingredient will be 10 milligrams per container and the final concentration of polysorbate 80 in the container will be 1% by weight. The mixture is dispensed into each can, the valves are crimped onto the can and the required amount of dichlorotetrafluoroethane is added under pressure.

Topical Formulation

An ointment for topical administration may be prepared by adding the active ingredient to a mixture of 48% by weight white petrolatum, 10% liquid petrolatum, 8% glycerol monostearate, 3% isopropYl myristate and 20% lanolin at 70° C. After thorough mixing, a warm solution of methyl and propyl parabens in water containing sodium acetone bisulfite is added such that the final concentrations of each paraben is 0.15%, of wafer is 8% and of sodium acetone bisulfite is 0.5%. The mixture is stirred until it has reached room temperature.

Phospholipase $A_2$ Inhibition Test System

The compounds of this invention have been shown to inhibit phospholipase $A_2$ in an in vitro test system using the porcine pancreatic $pLA_2$ enzyme and an assay modified from Hirata et al. (*Proc. Natl. Acad. Sci (USA)*, 77, 2533, 1980). The reaction was run in a total volume of 0.1 ml with the enzyme at a final concentration of 19 units/ml (0.025 µg protein/ml) which gave approximately 5000–8000 dpm (disintegration per minute) of activity in a buffer containing 25 mM Tris (trihydroxymethyl aminoethane), 25 mM glycylglycine, 25 mM $CaCl_2$ and 0.75 mM EDTA (tetra sodium salt), pH 8.5. The drug was added to the enzyme solution, incubated for 2 minutes, and the substrate, [arachidonyl-1-$^{14}$C]L-α-1-palmitoyl-2-arachidonyl phosphatidylcholine, at a final concentration of 7 µm (40,000 dpm), was then added to begin the reaction which proceeded for five minutes at 37° C. The reaction was stopped by freezing in a dry ice-ethanol slurry and the arachidonic acid products were separated from the unreacted substrate using silica gel columns.

All reactions were run in duplicate. Inhibitors were dissolved in 0.2 M Tris-Cl (trihydroxymethyl aminoethane hydrochloride), pH 8.5 or dissolved in DMSO and then diluted with Tris-Cl buffer (maximum DMSO concentration, 7%). The $IC_{50}$ was determined by inspection of a semilog plot of % inhibition versus final inhibitor concentration.

The enzyme phospholipase A$_2$ (pLA$_2$), catalyzes the release of fatty acids from the 2-position of phospholipids, particularly phosphatidyl choline. Arachidonic acid (AA) is most frequently found at the 2-position of phospholipids. Once it is released by the action of pLA$_2$, AA can be oxygenated by cyclooxygenases and lipoxygenases to the potent inflammatory mediators prostaglandins and leukotrienes, respectively. Inhibition of pLA$_2$ will block the generation of these local inflammatory mediators, thereby reducing inflammation. Since AA is the substrate for both cyclooxygenases and lipoxygenases, inhibition of pLA$_2$ will reduce the levels of both prostaglandins and leukotrienes. Many current anti-inflammatory drugs, e.g., salicylates, inhibit cyclooxygenases but not lipoxygenases, so that only prostaglandin levels are reduced.

TPA Inflammation Inhibition Test

The compounds of Formula (I) have been shown to be efficacious in murine models of skin inflammatory diseases. One such model is the inflammation induced by tetradecanoyl phorbol acetate (TPA), modified from the method of Kuehl et al., Nature, 1977, 265, 170; and Van Arman, Clin. Pharmacol. Ther., 1974, 16, 900. The TPA model mimics many of the inflammatory change which occur in human skin diseases such as psoriasis, since elevated levels of inflammatory arachidonic acid metabolites are found and an influx of polymorphonuclear leukocytes is observed. The test procedure used to evaluate the compounds of Formula (I) is as follows: the test compound (100 mg/ear) is applied to both ears of mice in an appropriate vehicle, such as acetone, and then the inflammatory stimulus (TPA) is applied to the right ear.

Four hours later, the edema is measured by removing standard size discs from the ears using a biopsy punch. A control group of animals receives TPA in vehicle applied to the right ear, and vehicle alone to the left ear. The weights of the ear discs are determined, and the suppression of swelling observed in animals treated with the test compound is determined. Results obtained in this model for selected compounds of Formula (I) are shown in Table III.

TABLE III

| Example | % Inhibition of Control Swelling |
| --- | --- |
| 7 | 21 |
| 21 | 31 |
| 37 | 20 |
| 52 | 40 |

"Consisting essentially of" in the present disclosure is intended to have its customary meaning; namely, that all specified materials and conditions are very important in practicing the invention but that unspecified materials and conditions are not excluded so long as they do not prevent the benefits of the invention from being realized.

What is claimed is:

1. A substituted benzylketone phospholipase A$_2$ inhibitor of the formula:

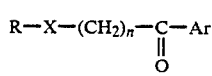

or a pharmaceutically acceptable salt thereof, wherein

Ar is

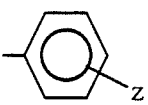

and Z is H, F, Cl, Br, OH, —OR$^1$, —S(O)$_m$R$^1$ and R$^1$ is methyl or ethyl, and m is 0, or 2;

n is 2 to 5;

X is NH, —NR$^2$, and R$^2$ is methyl or ethyl;

R is C$_6$–C$_{25}$ alkyl, aryl or substituted aryl of the formula:

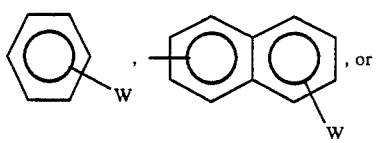

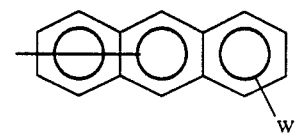

where W is H, F, Cl, Br, hexafluoroisopropanol, phenyl, C$_1$–C$_{18}$ alkyl, —OR$^3$, —SR$^3$, and R$^3$ is methyl or ethyl;

or R is benzhydryl, or C$_7$–C$_{25}$ alkaryl or substituted alkaryl where the substitution is on the aromatic moiety and is F, Cl, Br, OR$^3$, S(O)$_r$R$^3$, or C$_1$–C$_{10}$ alkyl, where R$^3$ is methyl or ethyl, and r is 0.1, or 2;

provided that:

a. when X is —NCH$_3$ or —NC$_2$H$_5$, R must be hydroxyhexafluoroisopropylphenyl;

b. when X is O, n cannot be 2;

c. when X is —S(O)$_p$, W cannot be methyl or ethyl;

d. when X is NH, R cannot be phenyl, benzyl, 1-methylbenzyl, phenylethyl, substituted phenylethyl, or pyridyl; and e. when R is benzhydryl, Z must be F.

2. A substituted benzylketone phospholipase A$_2$ inhibitor of claim 1, wherein

Ar is

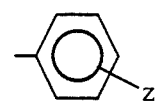

and Z is H, F, Cl, OH, —OR$^1$, —S(O)$_m$R$^1$, and R$^1$ is methyl or ethyl, and m is 0 or 2;

X is NH;

R is C$_6$–C$_{25}$ alkyl, aryl or substituted aryl of the formula:

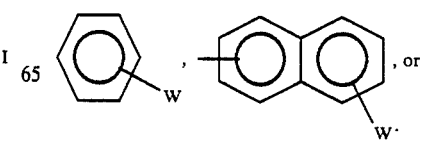

-continued

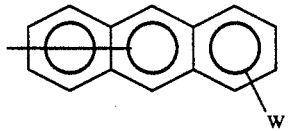

where W is H, hexafluoroisopropanol, phenyl, $C_1$–$C_{14}$ alkyl, —$OR^3$, or —$SR^3$, where $R^3$ is methyl or ethyl;

or R is 2-naphthalenylethyl, dehydroabietyl, 4-methoxy-1-naphthalenylmethyl, benzyl, 6-methoxy-2-naphthalenylethyl, 1-naphthalenylethyl, 1-naphthalenylmethyl, benzhydryl; provided that:

when X is NH, R cannot be pyridyl, and $R^3$ cannot be methyl or ethyl.

3. A substituted benzylketone phospholipase $A_2$ inhibitor of claim 2, wherein

Ar is phenyl, 4-fluorophenyl, 4-methoxyphenyl, or 4-methylthiophenyl;

n is 2 or 3;

X is NH;

R is 4-(hexafluoroisopropyl)phenyl, cyclohexane methyl, myrtanyl, 2-naphthalenylethyl, 1-naphthalenylethyl, 2-methylphenyl, 3-methylphenyl, 4-methylphenyl, hexyl, heptyl, octyl, decyl, undecyl, dodecylphenyl, tetradecyl, hexyldecyl, octadecyl, 4-tertbutylphenyl, 4-n-butylphenyl, 4-n-hexylphenyl, 4-decylphenyl, 4-dodecylphenyl, 6-methoxy-2-naphthalenylethyl, 4-methoxy-1-naphthalenylmethyl, 4-biphenylmethyl, dehydroabietyl, or 2-(1-adamantyl)ethyl, 1-methyl-1-(1-adamantyl)methyl;

provided that:

when X is NH, R cannot be 2-, 3-, or 4-methylphenyl, or 4-pyridyl,

4. The compound of claim 1 which is 1-(4-Fluorophenyl)-3-(undecylamino)-1-propanone Hydrochloride.

5. The compound of claim 1 which is 1-(4-Fluorophenyl)-3-(decylamino)-1-propanone Hydrochloride.

6. The compound of claim 1 which is 4-([1,4a-Dimethyl-1,2,3,4,4a,9,10,10a-octahydro-7-(1-methylethyl)-1-phenanthrenyl]-methylamino]-1-(4-fluorophenyl)-1-butanone 4-Methylbenzene sulfonate.

7. The compound of claim 1 which is 1-(4-Fluorophenyl)-3-([1,4a-dimethyl-7-(1methylethyl)-1,2,3,4,4a,9,10,10a-octahydro-1-phenanthrenyl-1-yl]methylamino]-1-propanone 4-Methylbenzene sulfonate.

8. A pharmaceutical composition, consisting essentially of a substituted benzylketone phospholipase $A_2$ inhibitor of claim 1 in an amount sufficient to provide anti-inflammatory or anti-allergic effects in a mammal suffering from a phospholipase $A_2$-mediated condition, and a pharmaceutically acceptable carrier.

9. A pharmaceutical composition, consisting essentially of a substituted benzylketone phospholipase $A_2$ inhibitor of claim 2 in an amount sufficient to provide anti-inflammatory or anti-allergic effects in a mammal suffering from a phospholipase $A_2$-mediated condition, and a pharmaceutically acceptable carrier.

10. A pharmaceutical composition, consisting essentially of a substituted benzylketone phospholipase $A_2$ inhibitor of claim 3 in an amount sufficient to provide anti-inflammatory or anti-allergic effects in a mammal suffering from a phospholipase $A_2$-mediated condition, and a pharmaceutically acceptable carrier.

11. A pharmaceutical composition, consisting essentially of the substituted benzylketone phospholipase $A_2$ inhibitor of claim 4 in an amount sufficient to provide anti-inflammatory or anti-allergic effects in a mammal suffering from a phospholipase $A_2$-mediated condition, and a pharmaceutically acceptable carrier.

12. A pharmaceutical composition, consisting essentially of the substituted benzylketone phospholipase $A_2$ inhibitor of claim 5 in an amount sufficient to provide anti-inflammatory and/or anti-allergic effects in a mammal suffering from a phospholipase $A_2$-mediated condition, and a pharmaceutically acceptable carrier.

13. A pharmaceutical composition, consisting essentially of the substituted benzylketone phospholipase $A_2$ inhibitor of claim 6 in an amount sufficient to provide anti-inflammatory or anti-allergic effects in a mammal suffering from a phospholipase $A_2$-mediated condition, and a pharmaceutically acceptable carrier.

14. A pharmaceutical composition, consisting essentially of the substituted benzylketone phospholipase $A_2$ inhibitor of claim 7 in an amount sufficient to provide anti-inflammatory or anti-allergic effects in a mammal suffering from a phospholipase $A_2$-mediated condition, and a pharmaceutically acceptable carrier.

15. A method of treating inflammatory or allergic conditions mediated by phospholipase $A_2$ in a mammal, comprising administering to the mammal a therapeutically effective amount of a substituted benzylketone phospholipase $A_2$ inhibitor of claim 1.

16. A method of treating inflammatory or allergic conditions mediated by phospholipase $A_2$ in a mammal, comprising administering to the mammal a therapeutically effective amount of a substituted benzylketone phospholipase $A_2$ inhibitor of claim 2.

17. A method of treating inflammatory or allergic conditions mediated by phospholipase $A_2$ in a mammal, comprising administering to the mammal a therapeutically effective amount of a substituted benzylketone phospholipase $A_2$ inhibitor of claim 3.

18. A method of treating inflammatory or allergic conditions mediated by phospholipase $A_2$ in a mammal, comprising administering to the mammal a therapeutically effective amount of the substituted benzylketone phospholipase $A_2$ inhibitor of claim 4.

19. A method of treating inflammatory or allergic conditions mediated by phospholipase $A_2$ in a mammal, comprising administering to the mammal a therapeutically effective amount of the substituted benzylketone phospholipase $A_2$ inhibitor of claim 5.

20. A method of treating inflammatory or allergic conditions mediated by phospholipase $A_2$ in a mammal, comprising administering to the mammal a therapeutically effective amount of the substituted benzylketone phospholipase $A_2$ inhibitor of claim 6.

21. A method of treating inflammatory or allergic conditions mediated by phospholipase $A_2$ in a mammal, comprising administering to the mammal a therapeutically effective amount of the substituted benzylketone phospholipase $A_2$ inhibitor of claim 8.

22. A pharmaceutical composition of claim 8 which is formulated for topical administration.

23. A pharmaceutical composition of claim 9 which is formulated for topical administration.

24. A pharmaceutical composition of claim 10 which is formulated for topical administration.

25. A pharmaceutical composition of claim 22 wherein the substituted benzylketone phospholipase $A_2$ inhibitor is 1-phenyl-3-([4a-dimethyl-7-(1-methylethyl)-

1,2,3,4,4a,9,10,10a octahydro-1-phenanthren-1-yl]methylamino)-1-propanone, or a pharmaceutically acceptable salt thereof.

26. A pharmaceutical composition of claim 22 wherein the substituted benzylketone phospholipase A$_2$ inhibitor is 3-([1,4a-dimethyl-1,2,3,4,4a,9,10,10a-octahydro7-(1-methylethyl)-1-phenanthrenyl]methylamino)-1-(4-fluorophenyl)-1-propanone, or a pharmaceutically acceptable salt thereof.

* * * * *